(12) United States Patent
Zhao

(10) Patent No.: US 7,758,806 B2
(45) Date of Patent: Jul. 20, 2010

(54) METHODS OF STERILIZING ELASTOMERIC SEALING ARTICLES

(75) Inventor: Xia Zhao, Malvern, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1001 days.

(21) Appl. No.: 11/508,553

(22) Filed: Aug. 23, 2006

(65) Prior Publication Data

US 2007/0053788 A1    Mar. 8, 2007

Related U.S. Application Data

(60) Provisional application No. 60/711,845, filed on Aug. 26, 2005.

(51) Int. Cl.
*A61L 2/07* (2006.01)
*A61L 2/08* (2006.01)

(52) U.S. Cl. .............. 422/22; 422/26; 422/28

(58) Field of Classification Search ........... 422/1, 422/22, 25, 26, 27, 28, 34; 604/181, 199; 522/150, 157
See application file for complete search history.

(56) References Cited

U.S. PATENT DOCUMENTS

| 3,853,622 | A | * | 12/1974 | Rutten ............ 134/25.4 |
| 4,144,154 | A | | 3/1979 | Zapp et al. |
| 4,664,275 | A | | 5/1987 | Kasai et al. |
| 5,540,876 | A | | 7/1996 | Larson et al. |
| 5,597,530 | A | | 1/1997 | Smith et al. |
| 6,090,081 | A | | 7/2000 | Sudo et al. |
| 6,331,174 | B1 | | 12/2001 | Reinhard et al. |
| 6,809,142 | B1 | | 10/2004 | Takeyama et al. |
| 6,822,015 | B2 | | 11/2004 | Muraki |

FOREIGN PATENT DOCUMENTS

| EP | 0164583 A2 | 10/1985 |
| EP | 0199356 A2 | 4/1986 |
| EP | 1227126 A1 | 7/2002 |
| GB | 2108943 A | 7/1982 |
| WO | 83/00158 A1 | 1/1983 |
| WO | 2005/032627 A1 | 4/2005 |
| WO | 2005/058377 A2 | 6/2005 |

OTHER PUBLICATIONS

Simmons, Anne, "Sterilisation of Medical Devices", Business Briefing: Medical Device Manufacturing & Technology, 2004, pp. 1-4.

* cited by examiner

*Primary Examiner*—Sean E Conley
(74) *Attorney, Agent, or Firm*—David M. Fortunato; The Webb Law Firm

(57) ABSTRACT

The present invention provides a method sterilizing butyl rubber/styrene butadiene rubber (SBR) articles used in syringes or medical containers, comprising irradiating the butyl rubber/SBR elastomeric copolymer rubber article with gamma irradiation, wherein the SBR elastomeric copolymer comprises about 5% to about 50% of the rubber composition on a basis of total weight of the composition; and then exposing the irradiated rubber composition to a sterilizing gas for a time period sufficient to sterilize the rubber composition. The irradiated, sterilized rubber composition of the present invention is capable of maintaining superior performance standards with respect to sealability, recoverability from stress and elasticity.

20 Claims, No Drawings

METHODS OF STERILIZING ELASTOMERIC SEALING ARTICLES

CROSS REFERENCE TO RELATED APPLICATIONS

This application claims the benefit of Provisional Application Ser. No. 60/711,845, filed on Aug. 26, 2005, the contents of which is hereby incorporated by reference.

BACKGROUND OF THE INVENTION

1. Field of the Invention

This invention relates to methods of sterilizing sealing articles used in syringes and other medical container devices by irradiating and autoclaving the same.

2. Description of Related Art

Elastomers are used in many important and critical applications in medical devices and pharmaceutical packaging. As a class of materials, their unique characteristics, such as flexibility, resilience, extendibility, and sealability, have proven particularly well suited for products such as catheters, syringe tips, drug vial articles, injection sites, tubing, gloves and hoses. Three primary synthetic thermoset elastomers typically are used in medical applications: polyisoprene rubber, silicone rubber, and butyl rubber. Of the three rubbers, butyl rubber has been the most common choice for articles due to its high cleanness and permeation resistance which enables the rubber to protect oxygen- and water-sensitive drugs.

Syringe plunger tips or pistons typically are made of a compressible, resilient material such as butyl rubber, because of the vulcanized rubber's ability to provide a seal between the plunger and interior housing of the syringe. Syringe plungers, like other equipment used in the care and treatment of patients, have to meet high performance standards, such as the ability to provide a tight seal between the plunger and the barrel of the syringe.

Many sterilization techniques are available today to sterilize medical devices to eliminate living organisms such as bacteria, yeasts, mold and viruses. Commonly used sterilization techniques used for medical devices include autoclaving, ethylene oxide (EtO) or gamma irradiation, as well as more recently introduced systems that involve low-temperature gas plasma and vapor phase sterilants.

One common sterilization technique is steam sterilization or autoclaving, which is a relatively simple process that exposes a device, for example, to saturated steam at temperatures of over 120° C. for a minimum of twenty minutes at a pressure of about 120 kPa (Booth, A. F. "Sterilization of Medical Devices," Buffalo Grove, Ill.: Interpharm Press, 1999). The process is usually carried out in a pressure vessel designed to withstand the elevated temperature and pressure to kill microorganisms by destroying metabolic and structural components essential to their replication. Autoclaving is the method of choice for sterilization of heat-resistant surgical equipment and intravenous fluid as it is an efficient, reliable, rapid, relatively simple process that does not result in toxic residues. However, autoclaving can lead to hydrolysis, softening or degradation of many biomedical polymers leading to unacceptable changes in mechanical properties (Anderson, J. M. et al., "Implants and Devices," Biomaterials Science, eds. Ratner, B. D. et al., Academic Press: London, pp. 415-420).

Radiation sterilization in the form of ionizing radiation commonly is used in hospitals for medical devices such as catheters, surgical items and critical care tools. Gamma irradiation is the most popular form of radiation sterilization and typically is used when materials are sensitive to the high temperature of autoclaving but are compatible with ionizing radiation. The bactericidal effect of gamma irradiation exerts its microbicidal effect by oxidinating biological tissue, and thus provides a simple, rapid and efficacious method of sterilization. Gamma rays are used either from a cobalt-60 ($^{60}$Co) isotope source or from a machine-generated accelerated electron source. Sufficient exposures are achieved when the materials to be sterilized are moved around an exposed $^{60}$Co source for a defined period of time. The most commonly used validated dose for sterilizing medical devices is 25 kGy (Booth, A. F. "Sterilization of Medical Devices," Buffalo Grove, Ill.: Interpharm Press, 1999). The use of gamma irradiation presents several disadvantages, however, including high capital costs and physical changes in some biomaterials, such as embrittlement, discoloration, odor generation, stiffening, softening, an increase or decrease in melt temperature and decreases in molecular weight.

Hence, despite the availability of a wide range of sterilization techniques, no single sterilization process is capable of sterilizing all medical devices without adverse effects which are caused mainly by incompatibilities between the material used in the medical device and sterilization process parameters. Syringe plunger tips made of pure butyl rubber can be autoclaved without adverse effects but they are not radiation stable, especially under stress conditions, resulting in the seal between the plunger tip and the interior housing of the syringe to be compromised causing leakage of the syringe contents.

There exists a need, therefore, to provide sterilization methods for medical devices such as syringe plunger tips using compositions which can withstand the process of sterilization and maintain high performance standards.

SUMMARY OF THE INVENTION

The present invention provides a method of sterilizing a rubber article, comprised of irradiating a rubber article, wherein the rubber article is prepared from a composition comprising butyl rubber and about 5% to about 50% by weight of an elastomeric copolymer on a basis of total weight of the composition; and exposing the irradiated rubber article to a sterilizing gas for a time period sufficient to sterilize the rubber article.

The present invention also provides a method of sterilizing a container and a rubber closure that are assembled or unassembled, comprised of irradiating the container and the rubber closure prior to exposing the container and rubber closure to a sterilizing gas for a time period sufficient to sterilize the container and rubber closure, wherein the rubber closure is comprised of a composition of butyl rubber and about 5% to about 50% by weight of an elastomeric copolymer on a basis of total weight of the composition.

The present invention further provides a method of sterilizing a prefilled container, comprised of filling a container with a therapeutic fluid or a non-therapeutic fluid, inserting a rubber closure into the container and irradiating the prefilled container prior to exposing the prefilled container to a sterilizing gas for a time period sufficient to sterilize the prefilled container, wherein the rubber closure is comprised of a composition of butyl rubber and about 5% to about 50% by weight of an elastomeric copolymer on a basis of total weight of the composition.

The present invention still further provides rubber articles and rubber closures comprised of preparing a composition of butyl rubber and about 5% to about 50% by weight of an elastomeric copolymer on a basis of total weight of the composition in which the rubber composition is crosslinked prior to irradiation.

DETAILED DESCRIPTION OF THE INVENTION

The present invention provides an improved method of sterilizing rubber articles that can be used, for example, as stoppers or syringe plunger tips for medical containers. The method comprises the steps of irradiating the rubber article with ionizing radiation, wherein the rubber article is prepared from a composition comprising butyl rubber and about 5% to about 50% by weight of an elastomeric polymer on a basis of total weight of the composition, and then exposing the irradiated rubber article to a sterilizing gas for a time period sufficient to sterilize the rubber article. Containers and rubber articles that are assembled, unassembled, or prefilled containers comprising such rubber articles can be sterilized by the same method.

As used herein, "assembled" containers and rubber articles refers to containers in which the rubber articles are inserted therein.

Suitable uses for the sterilized rubber articles or closures of the present invention include, without limitation, stoppers such as those used in syringe plunger tips or closures used to close the opening of medical evacuation blood collection containers.

The rubber article is prepared from at least one butyl rubber and at least one elastomeric polymer. Suitable butyl rubber useful in the method of the present invention includes copolymers of isobutylene (about 97-98%) and isoprene (about 2-3%). The butyl rubber can be halogenated with chlorine or bromine. Suitable butyl rubber vulcanizates can provide good abrasion resistance, excellent impermeability to gases, a high dielectric constant, excellent resistance to aging and sunlight, and superior shock-absorbing and vibration-damping qualities to articles formed therefrom.

The elastomeric copolymers that can be used in the present invention include, without limitation, styrene copolymers such as styrene-butadiene (SBR or SBS) copolymers, styrene-isoprene (SIS) block polymers or styrene-isoprene/butadiene (SIBS), in which the content of styrene in the styrene block copolymer ranges from about 10% to about 70%, and preferably from about 20% to about 50%.

Generally, styrene block copolymers (SBCs) consist of at least three blocks, namely, two hard polystyrene end blocks and one soft, elastomeric (polybutadiene, polyisoprene, either or not partially hydrogenated) midblock. Generally, the hard and soft blocks are immiscible so that, on a microscopic scale, the polystyrene blocks can form separate domains in the rubber matrix, thereby providing physical crosslinks in the rubber.

Suitable SBCs can be prepared by any suitable method known to one skilled in the art, such as anionic living polymerization with an organometallic catalyst, such as butyl-lithium, as an initiator. The molecular weight of SBCs typically ranges from about 100,000 to 300,000 g/mole.

In a non-limiting example, in non-polar media and for typical initiator concentrations and polymer molecular weights, the microstructure of the SBC midblocks can be about as follows: the butadiene midblock having 35% cis-1,4, 55% trans-1,4, and 9% 1,2 (vinyl) insertion; and the isoprene midblock having 70% cis-1,4, 25% trans-1,4, and 5% 1,2 or 3,4 (vinyl) insertion.

Because of the presence of double bonds in the polydiene midblocks, both SBS and SIS can be vulnerable to thermal and oxidative degradation. For polybutadiene, degradation typically occurs through crosslinking and for polyisoprene through chain scission. By selectively hydrogenating the midblock, SBCs can become substantially more stable. To improve thermo-oxidative stability, UV stability and/or tensile strength of the elastomeric copolymers of the present invention, they can be at least partially hydrogenated; i.e., hydrogenating about 10% to about 90% of the polydiene midblock double bonds.

Crosslinking of the rubber composition of the present invention can be carried out using a suitable crosslinking agent, such as, for example and without limitation, 1,1-di(t-butylperoxy)-3,3,5-trimethylcyclohexane, t-butylcumylperoxide, di-cumylperoxide, 2,5-dimethyl-2,5-di(t-butylperoxy)hexane or -hexin-3, t-butyl-peroxyisopropylcarbonate, benzoylperoxide, di-t-butylperoxide, 2,2'-di-t-butyl-peroxybutane, di-isobutylperoxide, 3-benzoylperoxy-3-methylbutyltriethysilane, pertrimellitic acid tri-t-butyl ester, 3,3',4,4'-tetra(t-butylperoxycarbonyl)-benzophenone, di-t-butylperoxide, t-butylperoxybenzoate or 2,5-di(t-butylperoxy)-2,5-dimethylhexane.

The proportion of the crosslinking agent in the rubber composition of the present invention can range from about 0.5% to about 5% by weight on a basis of total weight of the composition.

It is believed, without being bound by the theory, that the final processing step of gamma irradiation of the rubber composition of the present invention optimizes prior chemical curing of the rubber composition.

Additionally, the rubber composition of the present invention can include, without limitation, antioxidants and/or inorganic reinforcing agents to preserve the stability of the rubber composition.

Suitable antioxidants include, for example and without limitation, 2,6-di-t-butyl-p-cresol, n-octadecyl-.beta.-(4'-hydroxy-3',5'-di-t-butylphenyl)propionate or tetrakis[methylene-3(3',5'-d-t-butyl-4-hydroxyphenyl)propionate]methane, in a proportion ranging from about 0.05% to about 1% by weight on a basis of total weight of the composition. The addition of one or more antioxidants to the rubber composition of the present invention is desired because antioxidants are capable of interrupting the degradative process of auto-oxidation. Auto-oxidation is initiated by heat, light, mechanical stress, catalyst residues or reaction with impurities, resulting in discoloration, viscosity changes, char formation and/or cracking of organic materials, such as the rubber composition of the present invention.

Suitable inorganic reinforcing agents that can be added to the rubber composition of the present invention can include, for example and without limitation, silica type fillers, clays or titanium oxide, which are used to improve the thermal and electric conductivity during crosslinking of the rubber composition, resulting in uniform crosslinking and prevention of deformation of the rubber composition. The amount of the inorganic reinforcing agent added to the rubber composition can range from about 3% to about 7% by weight on a basis of total weight of the composition.

Suitable organic reinforcing agents that can be added to the rubber composition of the present invention can include, for example and without limitation, ultrahigh molecular weight polyethylene powder, polyethylene (PE), polypropylene (PP), polycarbonate (PC), polybutadiene (BR), 1,2-bonded styrene butadiene (SBR) or polysulfone type resins in a proportion ranging from about 20% to about 30% by weight on a basis of total weight of the composition.

The irradiated, sterilized rubber articles of the present invention is capable of maintaining superior performance standards with respect to sealability, recoverability from stress and elasticity compared to similar sterilized rubber compositions that have not been irradiated prior to sterilization.

For purposes of the present invention, containers are meant to include, but are not limited to, various medical devices and products, syringes, vials, evacuated blood collection tubes, cartridges, bottles and other containers of various sizes and shapes for containing a medium, in particular a fluid medium. The containers may be reusable or disposable, and may have a medical, veterinary, or non-medical purpose. The present invention is particularly directed to syringes.

Suitable sterilizing gases that can be used according to the methods of the present invention include, without limitation, steam or ethylene oxide.

Suitable containers that can be used in the present invention include, without limitation, containers which are radiation stable, that is, able to maintain their integrity with respect to properties such as strength, leakage, gas permeability and color, when subjected to irradiation. This may be accomplished by constructing the container out of a polyolefin composition which by its nature is radiation stable, or which includes additives in order to impart radiation stability to the polymer. For example, the container may be constructed of a cyclic olefin copolymer (COC), which by its nature is considered to be stable when exposed to ionizing radiation.

More desirably, the container may be constructed of a polyolefin composition which includes a radiation stabilizing additive to impart radiation stability to the container, such as a mobilizing additive which contributes to the radiation stability of the container. Particularly useful are radiation stable polymeric compositions prepared in accordance with U.S. Pat. Nos. 4,959,402 and 4,994,552, both of which are assigned to Becton, Dickinson and Company and both of which are incorporated in their entirety herein by reference.

The medium prefilled within the container of the present invention may be a therapeutic fluid or a non-therapeutic fluid, including materials such as flush solutions, contrast agents, pharmaceutical agents or vaccines. For example, the medium may be a saline solution, or may be a drug for parenteral administration to the body. After irradiating the prefilled container according to the methods of the present invention, the medium should maintain specific properties within the pharmacopoeia requirements, such as a pH between about 4.5 and about 7.0, ultraviolet absorbance of less than about 0.2 at a wavelength between 220 and 340 μm, and less than about 3.4 ppm of oxidizable substances.

In the present method, the rubber article, optionally in combination with an unfilled or prefilled container, is exposed to ionizing radiation. The ionizing radiation used to process the rubber composition, containers and or prefilled containers of the present invention can include, without limitation, gamma irradiation such as Cobalt 60 using any known gamma radiation device. The amount of gamma radiation depends on the amount of mass present and thus can range from about 10 kGy to about 60 kGy, preferably from about 35 to 55 kGy.

In the case of prefilled containers, they may be irradiated at any point after filling. Desirably, the container is sealed after being filled with the medium and prior to irradiation. In particularly desirable embodiments, the medical device is packaged within a separate container or package such as a blister pack, as is known in the art. In such case, gamma irradiation may be conducted on the device after it has been contained within the final packaging.

In the methods of the present invention, the irradiated rubber article container and/or prefilled container are exposed to sterilizing gas within a sterilization device, such as an autoclave device, sufficient to sterilize the article, container or prefilled container. The time period can range from about 30 to 40 minutes, in which the temperature of the steam is at least 120° C., but can range from about 120° C. to about 130° C., and in which the pressure within the autoclave can range from about 15 psi to about 30 psi. A suitable autoclave device that can be used according to the methods of the present invention includes, without limitation, the Vernitron 2000M autoclave manufactured by Alfa Medical.

The advantages of irradiating the rubber articles of the present invention prior to sterilization according to the methods provided herein include maintaining percentage strain of the rubber articles and preventing leakage over time.

As used herein, the phrase "percentage strain" is meant to refer to the degree of sealability, recoverability from stress and elasticity of the rubber composition used in the present invention. In particular, the percentage strain of a material quantifies the deformation of the elastomer after breaking apart, i.e., the higher the percentage strain, the greater the sealability, recoverability from stress and elasticity of the material.

The present invention is more particularly described in the following examples, which are intended to be illustrative only, as numerous modifications and variations therein will be apparent to those skilled in the art.

EXAMPLES

Example 1

Example 1 sets forth a comparative example demonstrating the autoclavability of butyl rubber/SBR syringe stoppers according to the present invention with and without prior irradiation processing, as determined by a Strain Measurement test. The purpose of the test is to quantify the degree of seal in a syringe as a function of stopper barrel interference; i.e., the degree of frictional force produced by the physical contact between a stopper and the inner wall of a syringe barrel; and to determine the ability of a syringe to maintain a seal for its shelf life by measuring percentage strain prior to assembly and percentage strain reduction over time, and then correlating these measurements with stopper leak test results.

A set of 10 each of rubber stoppers, 10 ml syringe barrels and plunger rods were provided for each of the following groups:

Group 1: control group—syringes and stoppers prepared from bromo butyl rubber and styrene-butadiene copolymer (manufactured by Helvoet Pharma) receiving no irradiation or autoclave sterilization;

Group 2: autoclave sterilization only; and

Group 3: irradiation prior to autoclave sterilization according to the methods of the present invention.

Also provided was a Micro-Vu Measuring System, a dial bore gage, a stopper holding pin for holding the plunger of the syringe and a v-block for holding the syringe barrel.

Group 2 consisted of filled syringes having stoppers according to the present invention inserted therein. In Group 3, irradiation was performed on unfilled syringes and stoppers using gamma irradiation in an amount ranging from 40-45 kGy, after which the syringes were filled and the stoppers inserted. The syringes and stoppers of Groups 2 and 3 then were autoclaved for 30 mins at 122° C.

Prior to inserting the stopper into the syringe barrel, the stopper outer diameter (OD) was measured across the front rib at two 90° planes using an optical comparator, the stopper was positioned on a threaded plunger rod that was placed on the stopper holding pin and the syringe barrel inner diameter (ID) was measured with the dial bore gage at two 90° planes.

Two strain test measurements were conducted: an initial test immediately after autoclaving Groups 2 and 3 (Time 0), and a second test 12 weeks later.

To calculate the percent strain of the material, the average stopper OD and barrel ID were calculated using the following equation:

Average=(0° measurement+90° measurement)/2

The interference (frictional force) and percentage strain of each syringe was calculated using the following equations:

Interference=Stopper *OD*−Barrel *ID*

% Strain=(Interference/Stopper *OD*)×100

The results of this test are provided in Table 1 below. The data show that at Time 0, the percent strain was 0.35% for stoppers autoclaved only (Group 2), 0.92% for stoppers subjected to irradiation processing prior to autoclaving according to the present invention (Group 3), and 2.91% for control stoppers (no irradiation or autoclave sterilization). Thus, compared to the controls, the stoppers that were autoclaved only exhibited a reduction of 88% in percentage strain. When the stoppers were irradiated prior to autoclaving, the reduction in percentage strain compared to the controls was 68%. Thus, although both Group 2 and Group 3 exhibited a reduction in percentage strain when compared to the control group, the rubber stoppers that were irradiated prior to autoclaving exhibited a 20% less decrease in percentage strain compared to the rubber stoppers that were not irradiated prior to autoclaving.

Twelve weeks post autoclaving, the percent strain was 0.65% for stoppers autoclaved only (Group 2) and 0.96% for stoppers irradiated prior to autoclaving (Group 3), which was a 78% reduction in percentage strain for stoppers that were autoclaved only compared to controls, and a 67% reduction in percentage strain for stoppers subjected to irradiation processing prior to autoclaving compared to controls. Thus, twelve weeks post autoclaving, the percentage strain exhibited by the rubber stoppers in Groups 2 and 3 increased from their initial values as measured at Time 0 by 46% and 1%, respectively.

This test demonstrates that irradiation processing prior to autoclave sterilization had a substantial effect on preserving the sealability, recoverability from stress and elasticity of the butyl rubber/SBR composition rubber stoppers of the present invention.

Example 2

Example 2 sets forth a comparative example demonstrating the autoclavability of butyl rubber/SBR syringe stoppers according to the present invention with and without prior irradiation processing, as determined by a Hand Breakloose Test. This test was performed to test the sealant properties of the butyl rubber/SBR stoppers.

A set of 70 each of rubber stoppers, 10 ml syringe barrels and plunger rods were provided for each of the three groups as described above in Example 1.

The test consisted of applying a slight forward pressure by hand to the plunger rod with the barrel tip of the syringe pointing upward in order to determine whether the rubber stopper seal remained intact or broke loose.

The results of this test are provided in Table 1 below. The data show that at Time 0, all of the rubber stoppers that were autoclaved only (Group 2) as well as the rubber stoppers that were irradiated prior to autoclaving (Group 3) were able to maintain their sealant properties, with none of the rubber stoppers breaking loose in response to the manual pressure. Twelve weeks post autoclaving, however, those stoppers from Group 2 (autoclaved only) had a fail rate of 38 out of 70, whereas those rubber stoppers from Group 3 (irradiation prior to autoclave sterilization) had a zero fail rate, and thus maintained their sealant properties.

This test demonstrates that those stoppers that were irradiated prior to autoclaving were able to maintain their sealant properties twelve weeks post autoclave sterilization, whereas over half of the stoppers that were autoclaved only lost their sealant property after twelve weeks.

Example 3

Example 3 sets forth a comparative example demonstrating the autoclavability of butyl rubber/SBR syringe stoppers according to the present invention with and without prior irradiation processing, as determined by a Pressure Leak test. This test was performed to test for fluid leakage past the rubber stopper seal of an assembled prefilled syringe.

A set of 70 each of rubber stoppers, 10 ml syringe barrels and plunger rods were provided for each of the three groups as described above in Example 1.

Also provided was a B-D/ISO pressure fixture (a fixture commonly used and known by those skilled in the art for exerting a specified pressure on an object, and which performs according to the standards of the International Standardization Organization), a pressure tank, a pneumatic line with regulator and gauge, weights and deionized water.

The prefilled syringes were inspected for fluid between the rubber stopper ribs prior to testing. The inspections were performed at about 18 inches with the naked eye under good lighting conditions.

At Time 0, the rubber stopper seal was broken loose (as described above in the "Break Loose" test) and any air bubbles from the rubber stopper face were dislodged by tapping the barrel gently with fingers. The syringe then was examined for fluid between the stopper ribs. Any syringe that had stopper leakage was not leak tested. With the sealing rib of the stopper aligned at the full volume scale reading, the plunger rod was oriented as viewed from the end with the ribs forming an "X" and not a "+", to achieve maximum plunger rod deflection relative to the axial position of the syringe. At the thumbpress end of the plunger rod, a side load weight was hung. The syringe was pressurized as follows: side load pressure was 3 newtons, side load weight was 306 grams; and internal pressure was 300 kPA or 43.5 psi. The pressure was held for 30 seconds. The edge of the rubber stopper front rib was placed at the maximum scale volume when the syringe was pressurized and the weight was hung. Care was taken that no air bubbles were in contact with the stopper face during the test.

The tested syringes were inspected for fluid leakage past the rubber stopper seal at the first rib of the rubber stopper. The syringes were removed from the pressure fixture and the tip caps were replaced. All syringes that failed the test were examined to determine the cause of the failure such as foreign matter in the seal area or a damaged rubber stopper.

The results of this test are provided in Table 1 below. The data show that at Time 0, all of the rubber stoppers that were autoclaved only (Group 2) as well as the rubber stoppers that were irradiated prior to autoclaving (Group 3) passed the test and did not leak fluid past the rubber stopper seal. Twelve weeks post autoclave sterilization, however, 15 out of 70 stoppers from Group 2 (autoclave only) leaked fluid past the stopper seal, whereas none of the stoppers from Group 3 (irradiation prior to autoclave sterilization) leaked fluid.

This test demonstrated, similar to the Hand Break Loose Test, that those rubber stoppers that were irradiated prior to autoclaving were able to maintain their seal twelve weeks post autoclave sterilization, whereas 21% of the stoppers that were autoclaved only lost their sealant properties after twelve weeks.

Example 4

Example 4 sets forth a comparative example demonstrating the autoclavability of butyl rubber/SBR syringe stoppers according to the present invention with and without prior irradiation processing, as determined by a Leakage Dye test. This test was performed to test the seal at the interface of the barrel and tip cap of syringe samples.

A set of 70 each of rubber stoppers, 10 ml syringe barrels and plunger rods were provided for each of the three groups as described above in Example 1. Also provided was a methyl blue dye (0.1%), a bell jar set-up with a vacuum pump and a pressure gauge.

The bell jar was filled with enough methyl blue dye to completely cover the syringe barrels. A wire was inserted into the inner diameter of an empty syringe barrel. A rubber stopper was inserted into the barrel three-quarters of the way down from the flange by venting with the wire to allow all excess air to escape. The wire then was removed from the syringe barrel. The syringes were placed in the bell jar, making sure they all were completely submerged in the methyl blue dye. The bell jar was evacuated to a residual pressure of 75 kPa±5 kPa (equivalent to 26.3 kPa, 3.8 psi or 7.7 inches of Hg of vacuum), which was maintained for 30 minutes. The vacuum chamber then was restored to atmospheric pressure and maintained for 30 minutes. The syringes then were removed from the dye solution but were not rinsed. The syringes were carefully dabbed with a paper towel to remove any dripping dye. Care was taken not to disturb or remove the tip caps. The inside of the barrel was visually examined for any trace of dye. If dye was observed inside the barrel, it was noted as a failure. The syringes were allowed to dry overnight up to 24 hours in a 140° F. (60° C.) oven. After drying, the tip cap was carefully unscrewed and the barrel taper and inner diameter of the tip cap was examined for any trace of dye. Observation of dye at the barrel taper and/or inner diameter of the tip cap constituted a failure.

The results of this test are provided in Table 1 below. The data show that at Time 0 as well as at 12 weeks post autoclave sterilization, all of the samples passed the test, with none of the barrel tapers or inner diameter of the tip caps of the syringe barrels from either Group 2 or Group 3 showing any trace of dye leakage.

This test demonstrates that all of the rubber stoppers had good sealant properties at the interface of the syringe barrel and tip cap of the syringe immediately subsequent to autoclave sterilization as well as after 12 weeks.

TABLE 1

| Sample Description | Sample # | | | | |
|---|---|---|---|---|---|
| | 1 Non-Sterile | 2 Autoclave Sterilization Only | | 3 Irradiation Processed and Autoclave Sterilization | |
| Age @ 40° C./ 75% RH | 0 | 0 | 12 wks | 0 | 12 wks |
| Strain, % | 2.91 | 0.35 | 0.65 | 0.92 | 0.96 |
| Hand Breakloose Test | NA | 0/70 Fail | 38/70 Fail | 0/70 Fail | 0/67 Fail |
| Pressure Leak Test | NA | 0/70 Fail | 15/70 Fail | 0/70 Fail | 0/67 Fail |
| Dye Leak Test | NA | 0/10 Fail | 0/10 Fail | 0/10 Fail | 0/10 Fail |

The present invention has been described with reference to specific details of particular embodiments thereof. It is not intended that such details be regarded as limitations upon the scope of the invention except insofar as and to the extent that they are included in the accompanying claims.

What is claimed is:

1. A method of sterilizing a rubber article, comprising the steps of:
   a) gamma irradiating a rubber article, wherein the rubber article is prepared from a composition comprising butyl rubber and about 5% to about 50% by weight of an elastomeric copolymer on a basis of total weight of the composition; and
   b) exposing the irradiated rubber article to a sterilizing gas comprising steam for a time period sufficient to sterilize the rubber article.

2. A method of sterilizing a container comprising the steps of:
   a) gamma irradiating a container comprising a container body and a rubber closure that are assembled or unassembled, wherein the rubber closure is prepared from a composition comprising butyl rubber and about 5% to about 50% by weight of an elastomeric copolymer on a basis of total weight of the composition; and
   b) exposing the irradiated container and rubber closure to a sterilizing gas comprising steam for a time period sufficient to sterilize the container and rubber closure.

3. A method of sterilizing a prefilled container, comprising the steps of:
   a) gamma irradiating a prefilled container comprising a container body, a rubber closure, and a fluid medium contained therein, wherein the rubber closure is prepared from a composition comprising butyl rubber and about 5% to about 50% by weight of an elastomeric copolymer on a basis of total weight of the composition; and
   b) exposing the irradiated prefilled container to a sterilizing gas comprising steam for a time period sufficient to sterilize the prefilled container.

4. The method of claim 1, wherein the rubber article is a rubber closure.

5. The method of claim 1, wherein the rubber article is a stopper.

6. The method of claim 1, wherein the rubber article is a syringe tip stopper.

7. The method of claim 1, wherein the butyl rubber is selected from the group consisting of bromo butyl rubber and chloro butyl rubber.

8. The method of claim 1, wherein the elastomeric copolymer is selected from the group consisting of styrene-butadiene copolymer (SBS), styrene-isoprene copolymer (SIS) and styrene-isoprene/butadiene copolymer (SIBS).

9. The method of claim 1, wherein the elastomeric copolymer is styrene-butadiene copolymer.

10. The method of claim 9, wherein the percentage of styrene in the styrene-butadiene copolymer ranges from about 20% to about 50% on a basis of total weight of the copolymer.

11. The method of claim 9, wherein the styrene-butadiene copolymer is partially hydrogenated.

12. The method of claim 1, wherein the composition further comprises a crosslinking agent.

13. The method of claim 1, further comprising the step of chemically crosslinking the composition prior to irradiation.

14. The method of claim 1, wherein the composition further comprises at least one member selected from the group consisting of antioxidants and inorganic reinforcing agents.

15. The method of claim 1, wherein the sterilizing gas is steam.

16. The method of claim 1, wherein the time period to which the irradiated rubber article is exposed to the sterilizing gas ranges from about 30 to about 40 minutes.

17. The method of claim 1, wherein the temperature of the sterilizing gas ranges from about 120° C. to about 130° C.

18. The method of claim 1, wherein in step (b), the irradiated rubber composition is exposed to the sterilizing gas at a pressure of about 15 psi to about 30 psi.

19. The method of claim 1, wherein the sterilizing gas is at a temperature of at least about 120° C. and the irradiated rubber composition is exposed to the sterilizing gas at a pressure of about 15 psi for a time period of at least about 30 minutes.

20. The method of claim 1, wherein the rubber composition is irradiated in an amount ranging from about 10 kGy to about 60 gKy.

* * * * *